(12) United States Patent
Siepmann

(10) Patent No.: US 6,197,256 B1
(45) Date of Patent: Mar. 6, 2001

(54) DEVICE FOR ANALYZING FLUID SAMPLES

(75) Inventor: Friedrich Wilhelm Siepmann, Gross-Umstadt (DE)

(73) Assignee: ISCO Inc., Lincoln, NE (US)

(*) Notice: Subject to any disclaimer, the term of this patent is extended or adjusted under 35 U.S.C. 154(b) by 0 days.

(21) Appl. No.: 09/077,542

(22) PCT Filed: Nov. 21, 1996

(86) PCT No.: PCT/EP96/05139

§ 371 Date: Nov. 16, 1998

§ 102(e) Date: Nov. 16, 1998

(87) PCT Pub. No.: WO97/21088

PCT Pub. Date: Jun. 12, 1997

(30) Foreign Application Priority Data

Dec. 1, 1995 (DE) ............................... 195 44 851
May 3, 1996 (DE) ............................... 196 17 707

(51) Int. Cl.[7] .................................................. G01N 31/22
(52) U.S. Cl. ..................... 422/79; 422/68.1; 422/78; 422/81; 436/62; 435/286.1; 435/286.5; 435/286.6; 435/287.1; 435/287.5
(58) Field of Search ............................. 422/68.1, 78, 79, 422/81, 106; 436/62, 180; 73/864.61, 864.34, 170.29, 170.34; 435/286.1, 287.1, 286.5, 286.6, 287.5

(56) References Cited

U.S. PATENT DOCUMENTS

| 4,089,209 | 5/1978 | Grana et al. |
|---|---|---|
| 4,314,969 | * 2/1982 | Arthur et al. ........................ 422/68 |
| 4,763,537 | * 8/1988 | Scott et al. ....................... 73/170 A |
| 5,197,340 | * 3/1993 | Jones ................................ 73/864.35 |
| 5,695,719 | * 12/1997 | Lynggaard et al. ................ 422/81 |
| 5,708,220 | * 1/1998 | Burge ............................. 73/864.34 |
| 5,993,742 | * 11/1999 | Binz et al. .......................... 422/81 |

* cited by examiner

Primary Examiner—Jill Warden
Assistant Examiner—Kalh Bex
(74) Attorney, Agent, or Firm—Burns, Doane, Swecker & Mathis, L.L.P.

(57) ABSTRACT

An analyzing system for analyzing fluid samples includes a measuring buoy immersible in a body of fluid to be tested. The buoy forms a sample chamber in which samples of the fluid are to be tested. The sample chamber communicates with a settling chamber through a chamber opening, and the settling chamber communicates with the body of fluid through a floor opening formed in the buoy below the chamber opening. A gas exchange apparatus communicates with the sample chamber and with a source of air or gas for introducing the air or gas into the sample chamber to drain sample fluid therefrom, and for discharging the air or gas from the sample chamber to admit sample fluid into the sample chamber from the settling chamber. A testing device is disposed in the sample chamber for testing the sample fluid, and is connected to a control and analysis device.

13 Claims, 6 Drawing Sheets

DEVICE FOR ANALYZING FLUID SAMPLES

BACKGROUND OF THE INVENTION

The invention relates to a device for analyzing fluid samples consisting of a sample chamber containing at least one testing device, which comprises a control and analysis device and a filling and draining device, through which, respectively, a fluid sample taken from a quantity of fluid is fed into the sample chamber and removed from it.

A typical area of application for such testing equipment is in waste water analysis. In this type of application, a fluid sample is taken from the waste water and tested in the sample chamber. Frequently, a reagent is added in the sample chamber and its reaction with the fluid sample is completed and measured. Gas-selective or ion-selective sensors, pH sensors, photo-optical sensors, and other sensors are commonly used for tests performed inside the sample chamber. A gaseous reaction product which develops during the reaction can be fed into a measuring device designed specifically for measuring this product, such as a $CO_2$ detector (published journal article by M. Levermann, "TOC Testing in an On-line Process", publication "Chemie, Umwelt, Technik" [Chemistry, Environment, Technology], 94, pages 12–15).

To fill the sample chamber, the fluid sample must be conveyed from the available quantity of fluid, such as waste water, through a supply line An unavoidable feature of such testing, particularly of waste water samples, is that deposits form in the fluid lines used to fill and drain the sample chamber. Unless they are routinely flushed—a relatively expensive procedure—there is a risk that these lines may become clogged.

Consequently, the objective of the invention is to design a device of the type specified initially in such a way that the sample chamber can be easily filled and drained without running the risk of clogging the fluid lines and incurring the substantial expense of rinsing.

SUMMARY OF THE INVENTION

According to the invention, this objective is solved in that the sample chamber is arranged in a measuring buoy immersible in a quantity of fluid and is connected to the outside of the measuring buoy via a chamber opening, that at least one testing device is arranged in the measuring buoy, and that the filling and draining device exhibits a gas exchange apparatus with which a gas which displaces the fluid sample is fed into and removed from the sample chamber.

Moving the sample chamber from a measuring device located outside the fluid to a measuring buoy immersible in the quantity of fluid eliminates the need for fluid lines which tend to become clogged. The sample chamber located inside the fluid being tested can be directly filled and drained without the need for any fluid lines.

As at least the section of the measuring buoy that contains the sample chamber is immersed into the fluid being tested, removing the gas in the sample chamber is sufficient for filling the sample chamber, i.e., by opening the sample chamber to the atmosphere, in the simplest case. The hydrostatic pressure of the fluid surrounding the measuring buoy forces the fluid sample into the sample chamber. To empty the sample chamber, a pressurized gas, such as air, is supplied by the gas exchange device to press the fluid sample out of the sample chamber. The intensity of the gas supply can be chosen so as to produce turbulence in the fluid sample in the sample chamber, thereby effectively rinsing and cleaning the sample chamber and the chamber opening with very simple means. This essentially eliminates clogging of the chamber opening.

The control and analysis device can be positioned in a remote location relative to the measuring buoy and be linked to the buoy by cables or lines. If need be, reagents and/or gases are—in addition to electric measuring signals and, if applicable, electric control impulses or an electric power supply—transported via lines that connect the measuring buoy with the remotely placed control and analysis device. Compared to the transport of fluid samples, the transport of these materials is completely unproblematic and does not lead to the risk of contamination or clogging. Alternatively, the control and analysis device can also be arranged in the measuring buoy.

Preferably, at least one reagent dosing device, which opens into the sample chamber and is connected to a reagent source located outside the measuring buoy via a hose assembly, is arranged in the measuring buoy. As a result, the types of tests that require the chemical reaction of the fluid sample with one or more reagents—which is often the case in waste water analysis—can also be performed in the sample chamber. As there is no risk of the transport lines for fluids or gaseous reagents becoming clogged, these lines can also be installed across relatively large distances between the measuring buoy and a supply unit.

Preferably, the gas exchange device exhibits a gas pump arranged in the measuring buoy and connected to the sample chamber which can be connected to a gas source located outside the measuring buoy via a hose assembly. As this type of hose assembly is also not subject to the risk of clogging, it can easily be installed across larger distances.

According to a preferred embodiment of the invention, the sample chamber opening may open into a settling chamber with a hole in its bottom which is arranged underneath the sample chamber in the measuring buoy. It may be necessary to separate the solid matter component prior to analysis, particularly when analyzing the aqueous component of activated sludge in a sewage treatment plant. The settling chamber connected upstream from the sample chamber is used to hold the fluid sample during a filling pause, so that the activated sludge settles or concentrates in the lower portion of the settling chamber before the fluid sample, which has been pre-cleaned in this manner, is allowed to enter the sample chamber.

To control this filling process over time, a fill level sensor is preferably positioned near the chamber opening connecting the settling chamber to the sample chamber and is connected to the control unit for the gas exchange device. The fill level sensor is used to determine when the settling chamber is full. When this occurs, the filling process is interrupted so that the sludge component can settle in the settling chamber. This filling process is resumed once this preset time period has expired.

To analyze activated sludge in which gas bubbles are constantly rising, it has proven to be advantageous to place a deflection object at a distance from the floor opening of the settling chamber which extends beyond the perpendicular projection of the perimeter of the floor opening on all sides. This deflection object prevents gas bubbles from entering the settling chamber and the sample chamber.

According to another advantageous embodiment of the invention, the sample chamber is linked to a gas supply line for a reaction gas, the chamber opening can be locked by means of a valve, and a gas discharge line with a locking valve runs from the sample chamber to an analysis device located at a distance from the measuring buoy. This makes it possible to subject the fluid sample drawn into the sample chamber to a reaction with the reaction gas when the chamber opening is locked, and to subsequently remove this reaction gas from the measuring buoy and convey it to a remotely positioned analysis device, so that the necessary analysis can be completed there.

BRIEF DESCRIPTION OF THE DRAWINGS

Illustrative examples of the invention which are depicted in the drawing are explained in greater detail below.

FIG. 2 depicts a section along line II—II in FIG. 1, while

DETAILED DESCRIPTION OF PREFERRED EMBODIMENTS OF THE INVENTION

Figure 1:
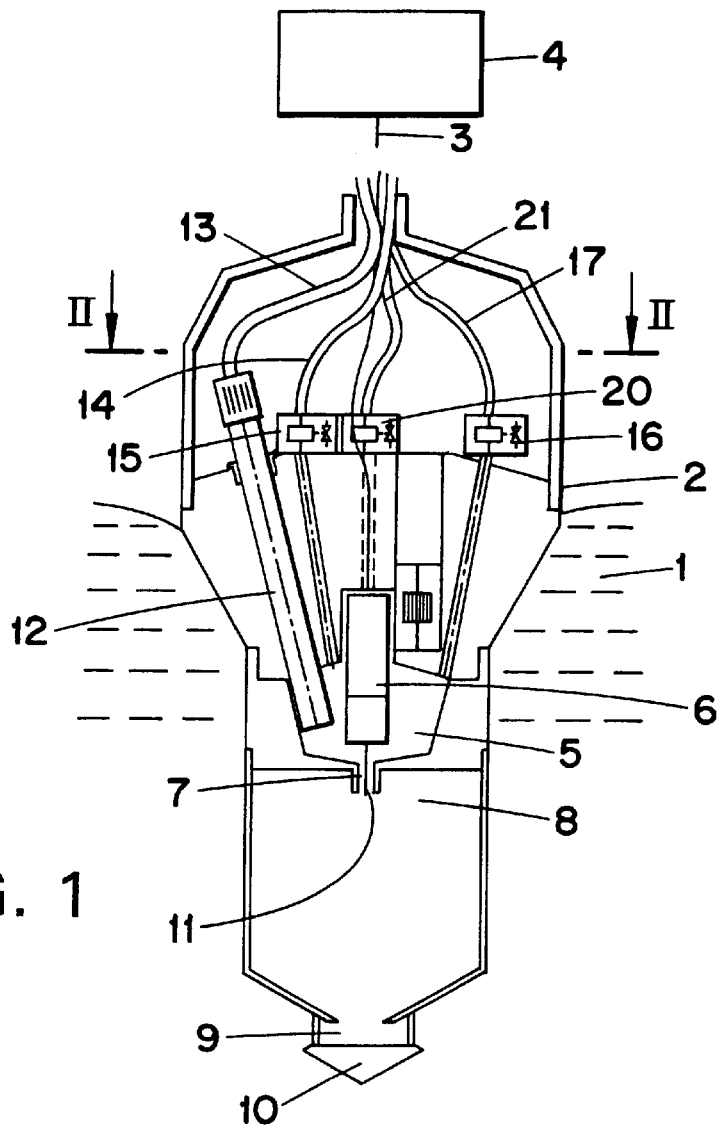
FIG. 1 depicts, in a vertical section, a device for measuring the $NH_4$ content of waste water.
Figure 2:
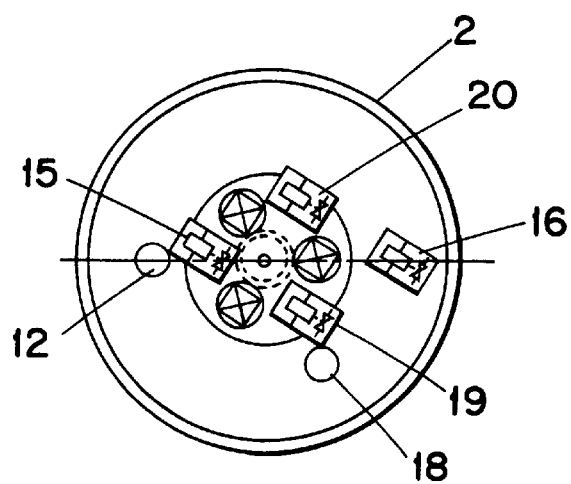

The device for measuring the $NH_4$ content of water depicted in FIGS. 1 and 2 exhibits a measuring buoy 2 immersible in the waste water 1 being tested which is connected, via schematically indicated lines 3, to a remotely positioned control and analysis device 4. A sample chamber 5 is arranged in the measuring buoy 2 which contains the waste water sample to be tested. A stirring apparatus 6 protrudes into the sample chamber 5. The sample chamber 5 has a chamber opening 7 in its floor through which the sample chamber 5 can be filled and emptied. A settling chamber 8 with a volume which exceeds that of the sample chamber is positioned below the chamber opening 7 in the measuring buoy 2. The settling chamber 8 has a floor opening 9, under which a deflection object 10 is positioned at a distance. The deflection object 10 extends beyond the perpendicular projection of the perimeter of the floor opening 9 on all sides, thereby preventing rising gas bubbles from entering the settling chamber 8 through the floor opening 9. A fill level sensor 11 is positioned near the chamber opening 7 that connects the settling chamber 8 with the sample chamber 5.

In the illustrative example depicted in FIGS. 1 and 2 a testing device invention of, an $NH_3$ probe 12, which is connected to the control and analysis device 4, protrudes into the sample chamber 5. A hose assembly 14 leads from a reagent source (not depicted) positioned outside the measuring buoy 2 to a solenoid valve 15, which forms a reagent dosing device for delivering a reagent into the sample chamber 5. In an analogous manner, a hose assembly 17 with a locking solenoid valve 16 is used to deliver calibration standard to the sample chamber 5.

A pH probe 18, which also protrudes into the sample chamber 5, is used to measure the pH value in the fluid sample. An air line, which contains a solenoid valve 19, also opens into the sample chamber 5.

To analyze a waste water sample, the sample chamber 5 and the settling chamber 8 are emptied by adding air or gas, which is achieved by opening the solenoid valve 19. When a solenoid valve 20 also connected to the sample chamber 5 is opened, the air contained in the sample chamber 5 and in the settling chamber 8 escapes through a hose assembly 21, and the settling chamber 8 is filled until the fill level sensor is activated. After a settling pause, during which the sludge component in the fluid sample and, if applicable, other precipitable substances have settled to the bottom of the settling chamber 8, the solenoid valve 20 is reopened and the effects of the hydrostatic pressure of the surrounding waste water result in the filling of the sample chamber 5.

Then the solenoid valve 15 is opened, allowing caustic solution to flow into the sample chamber 5 until the pH level at the probe 18 has reached a value of about 11. At a pH level of 11, the entire $NH_4$, once adequately mixed, is present in the form of $NH_3$ and is measured by the $NH_3$ probe 12 and subsequently analyzed by a computer in the control and analysis device 4. A new measuring cycle can then be performed as described above.

To calibrate the system, a standard line 17 can be connected to the sample chamber 5 via a solenoid valve 16, thus allowing a standard fluid to be fed into the chamber and an automatic calibration to be performed.

An $NO_3$ measuring device (not depicted) may be similarly equipped. In this case, an $NO_3$ probe replaces the $NH_3$ probe 12 described above. Furthermore, an additional conductivity probe is mounted in the sample chamber 5.

In each of the following illustrative examples, the same reference codes that are used in FIGS. 1 and 2 are used to designate identical parts.

Figure 3:
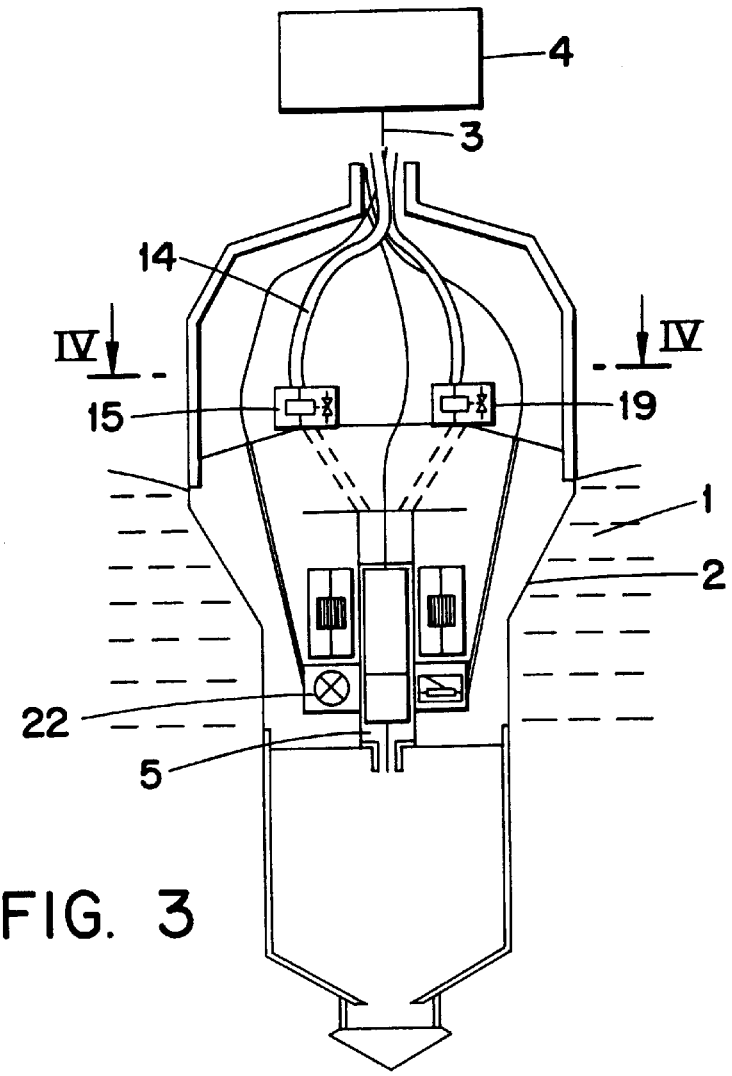
FIGS. 3 and 4 depict, in a representation corresponding to FIGS. 1 and 2, a device for measuring the nitrate or phosphate content of a waste water sample.
Figure 4:
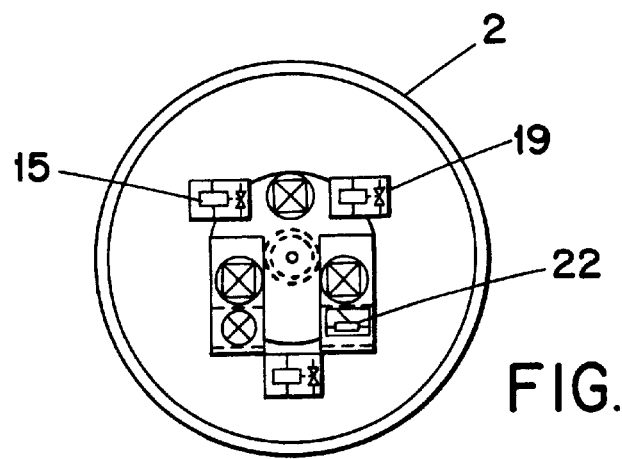

FIGS. 3 and 4 depict, in an illustrative example of the invention, a device for measuring the nitrate-phosphate content of waste water. An optical measuring cell 22, which transmits a signal to the control and analysis device 4 when a color change occurs in the fluid sample as a result of the measured addition of reagent through the hose assembly 14 and the solenoid valve 15, is arranged in the sample chamber 5.

Figure 5:
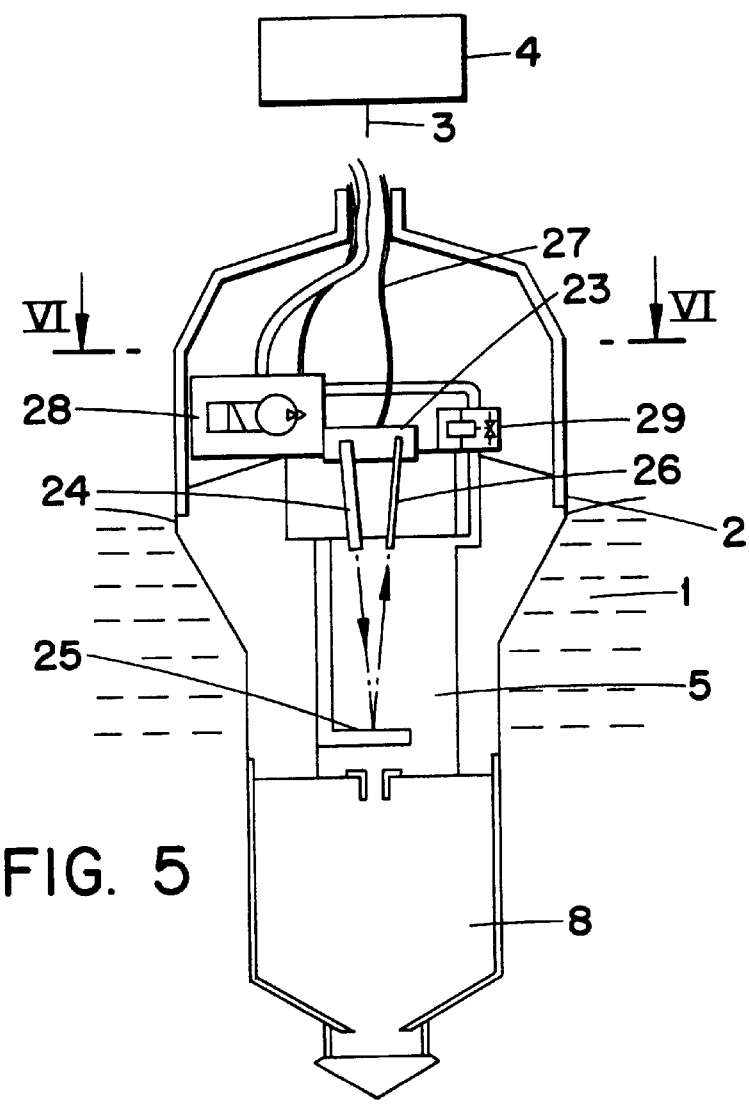
FIGS. 5 and 6 depict, in representations corresponding to FIGS. 1 and 2, a device for measuring the nitrate content of waste water.
Figure 6:
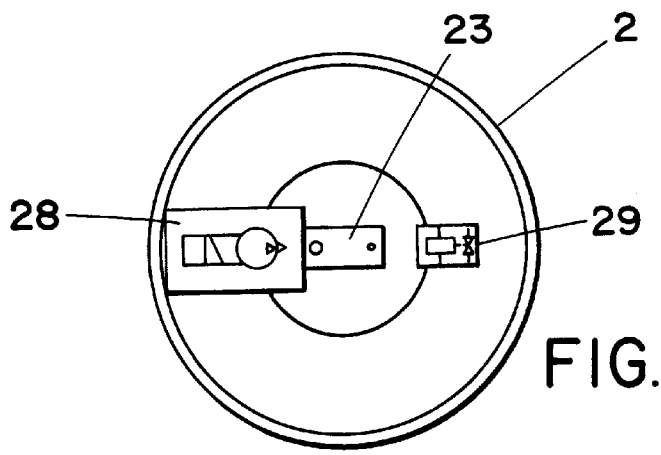

FIGS. 5 and 6 depict a device for measuring the nitrate content of waste water by means of an optical measuring device 23 which is arranged in the measuring buoy 2. A fiber optic transmitter 24 projects a light beam onto a reflector 25 in the sample chamber 5, where it is reflected and strikes a fiber optic receiver 26. The electric power needed to drive the optical device 23 and to transmit the signal to the control and analysis device 4 is provided through electric cables 27. A compressor 28, which is connected to the sample chamber 5 via a solenoid valve 29, serves as a gas exchange apparatus for filling and emptying the sample chamber 5 and the settling chamber 8. Once the sample chamber 5 has been drained, a reference reading can be taken to compensate for the signal changes attributable to dirt particles on the fiber optic transmitter 24, on the reflector 24 and/or on the fiber optic receiver 26.

Figure 7:
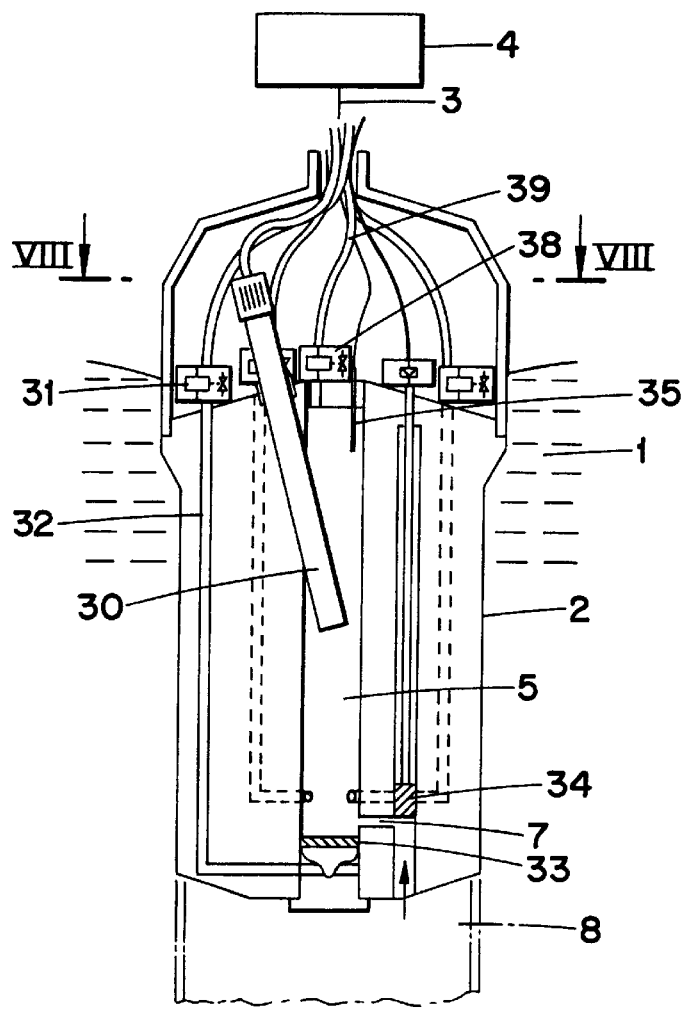
FIGS. 7 and 8 depict, in representations corresponding to FIGS. 1 and 2, a device for measuring the TOC content of waste water.
Figure 8:
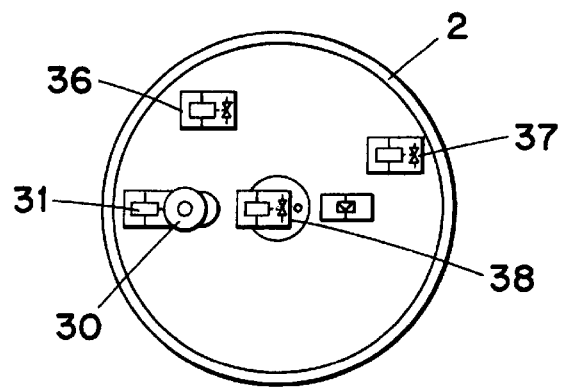

The illustrative example of the invention depicted in FIGS. 7 and 8 represents a device for analyzing the oxidizable carbon content (TOC content) of waste water. In this case, the measuring buoy 2 is also immersed in the waste water 1. A pH probe 30 protrudes into the sample chamber 5.

To feed reaction gas ($O_3$) into the sample chamber 5, a gas feed line 32 lockable with a solenoid valve 31 opens into the floor of the sample chamber 5 underneath a frit 33. To prevent the reaction gas being fed into the sample chamber 5 from evacuating the sample chamber 5, a valve 34 positioned near the chamber opening 7 is closed when reaction gas is fed into the sample chamber 5.

A fill level sensor 35 protruding into the sample chamber 5 emits a signal when the sample chamber 5 is completely full. Acid or alkaline solutions can be fed into the sample chamber 5 through solenoid valves 36 and/or 37. Once it has reacted with the waste water sample in the sample chamber 5, the reaction gas passes through a solenoid valve 38 and a gas removal line 39 and is conveyed to an analysis apparatus arranged in a control and analysis device positioned at a distance from the measuring buoy 2. The analysis of the discharged reaction gas performed there yields a reading for the TOC content of the waste water being analyzed.

In FIG. 7, a settling chamber 8 is indicated by dash-dot lines in the lower portion of the measuring buoy 2. This is meant to suggest that this type of settling chamber 8 can be eliminated. It may be necessary, particularly during TOC analysis, to eliminate the settling of solid matter components in the waste water under analysis if these solid matter components must also be considered when measuring the TOC content.

Figure 9:
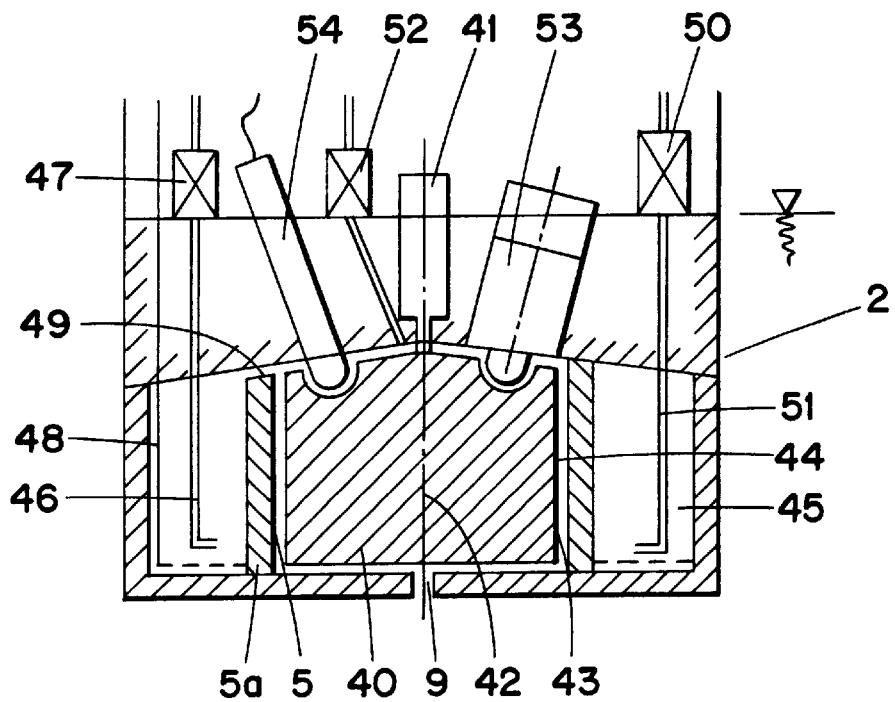
FIG. 9 depicts, in a simplified vertical section, a device for measuring the biological oxygen requirement (BSB) of a waste water sample.

The device depicted in FIG. 9 is used to determine the biological oxygen requirement (BSB) of waste water. The device is designed as a measuring buoy 2 immersible in the waste water. A drivable rotor 40 arranged in the sample chamber 5 is propelled to rotate around the vertical axis 42 by a motor 41. The outer surface 43 of the rotor 40 forms a biological growth surface. There is only a small gap 44, which forms the reaction chamber, between the outer surface 43 of the rotor 40 and the wall 5a of the sample chamber 5.

The sample chamber 5 is in direct contact with the surrounding fluid via the chamber opening 9 in the floor. The sample chamber 5 is surrounded by an aeration chamber 45, which serves to ventilate and temper the dilution water being used. To this end, an aerator 46, which is connected to an air supply valve 47, and a heater 48 project into the aeration chamber 45. The aeration chamber 45 opens into the sample chamber 5 through an overflow opening 49. Dilution water is fed into the aeration chamber 45 through a line 51 and a supply device 50, which may be featured as either a pump or a valve.

Once a test has been completed, the tempered dilution water is aerated in the aeration chamber 45. As this occurs, the air is discharged from the measuring buoy 2 through the overflow opening 49, the upper portion of the sample chamber 5, and through an air discharge valve 52.

Following sufficient aeration, the air supply valve 47 is closed and the valve 50 for the water supply is opened. As soon as a sufficient fill level is registered by a contact maker, the air discharge valve 52 is closed.

The tempered and aerated dilution water now displaces the waste water mixture from the preceding test in the sample chamber 5, and it is discharged through the chamber opening 9. A new test begins as soon as the waste water mixture in the sample chamber 5 has been replaced with dilution water. Waste water is then sucked into the sample chamber 5 by a dosing pump 53. An oxygen probe 54 is used to determine the oxygen consumption per unit of time and, consequently, the BSB.

The use of the rotor 40 as the carrier of the biological growth surface ensures that this growth surface comes into homogeneous contact with all of the sample in the sample chamber 5. The fact that the volume of the sample chamber 5 is very small may be considered particularly advantageous in this regard.

Figure 10:
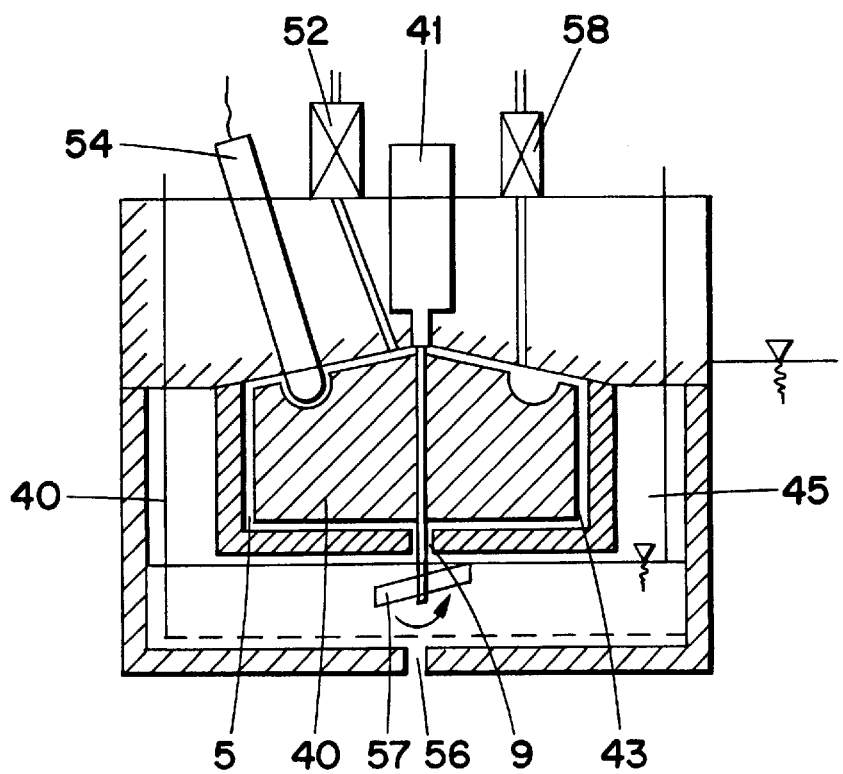
FIG. 10 depicts, in a simplified vertical section, another embodiment of a device for measuring the BSB of a waste water sample.

The device for determining the BSB depicted in FIG. 10 differs primarily from the device described above in that it operates without dilution water. In this case, a rotor 40 drivable by the motor 41 is also arranged in the sample chamber 5. Its outer surface 43 forms the biological growth surface. The chamber opening 9 in the floor of the sample chamber 5 opens into an aeration chamber 45, which surrounds both the floor and the perimeter of the sample chamber 5. This aeration chamber 55 has an opening 56 for the waste water in its floor. The rotor 40 is connected to an aerator 57 which protrudes into the aeration chamber 45. A line connected to an air supply valve 58 feeds into the sample chamber 5. The remaining parts are identified by the same reference numbers used to designate identical parts in FIG. 9.

The sample chamber 5, which forms the reaction chamber, and the aeration chamber 45 are evacuated by air flowing in through the valve 58. Then the hydrostatic pressure of the surrounding waste water forces waste water through the opening 56 and into the aeration chamber 45, where it is aerated and tempered. The aerated waste water is then pressed into the sample chamber 5 through the chamber opening 9. The oxygen probe 54 measures oxygen consumption per unit of time and converts this value into the biological oxygen requirement (BSB).

Figure 11:
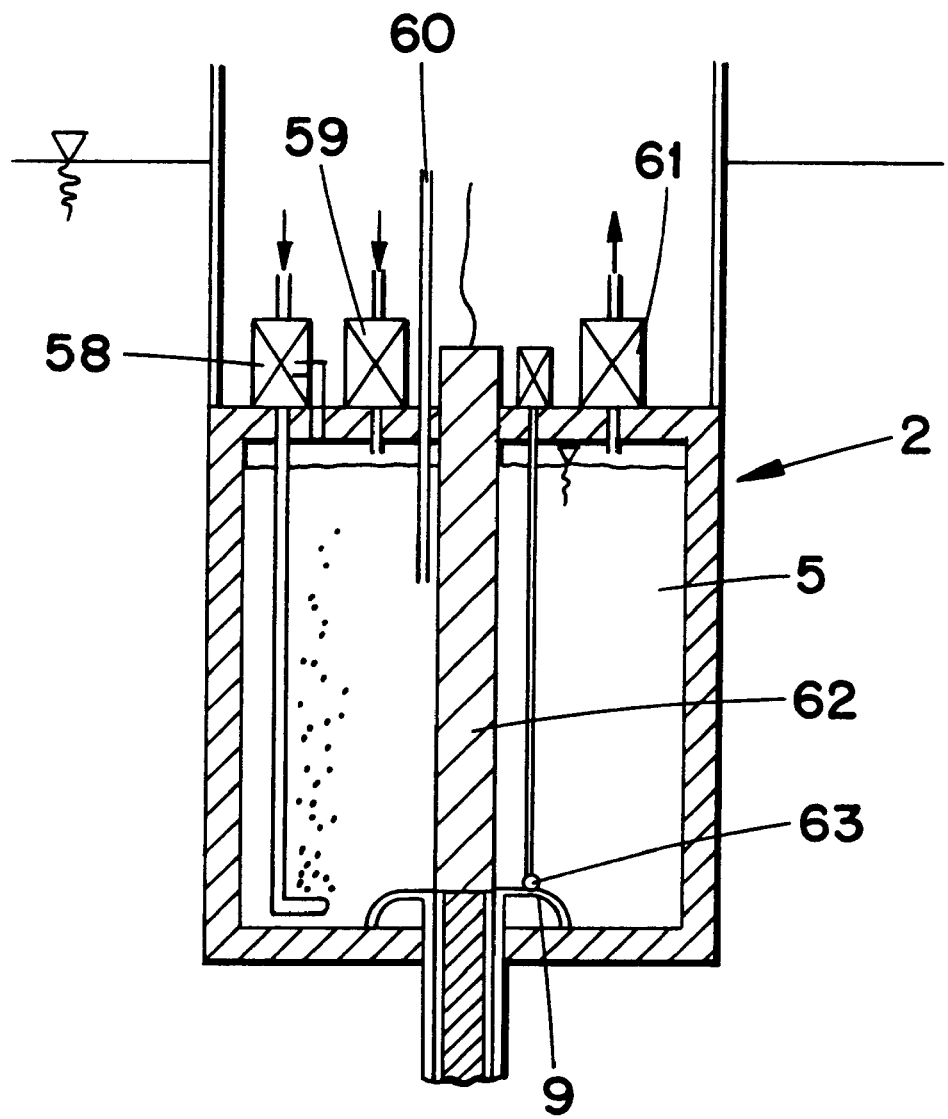
FIG. 11 depicts a device for measuring the chemical oxygen requirement (CSB) of a waste water sample, also presented in a simplified vertical section similar to the previous figures.

FIG. 11 depicts a device for determining the chemical oxygen requirement (CSB) featured as an immersible measuring buoy. An air or ozone supply line which is lockable by means of a valve 58 opens into the sample chamber 5. Reagents can be supplied through a reagent valve 59. A pH probe 60 protrudes into the sample chamber 5. Air or ozone can be evacuated from the sample chamber 5 through a discharge valve 61. An ozone measuring probe 62 is used to determine the ozone content. The chamber opening 9 of the sample chamber 5 is lockable by means of a valve 63.

The sample chamber 5 is filled when the intake valve 58 and the discharge valve 61 are open. The pH level is set to a preset value ranging from 3 to 5.

The waste water in the sample chamber 5 is gassed with ozone. After a sufficient amount of gassing has taken place, the ozone generator (not depicted) is switched off. Once the intake valve 58, which is featured as a three-way valve, has been switched, preset amounts of air or oxygen only are forced through the valve and against the surface of the water. When valve 63 is open, the ozone consumption per unit of time measured at the chamber opening 9 represents a measure for the CSB. Testing is repeated once the chamber has been emptied.

What is claimed is:

1. Apparatus for analyzing fluid samples comprising:
    a measuring buoy immersible in a body of fluid to be tested, the buoy forming a sample chamber in which samples of the fluid are to be tested, and a settling chamber, the sample chamber communicating with the settling chamber through a chamber opening, and the settling chamber communicating with the body of fluid through a floor opening formed in the buoy below the chamber opening;
    a gas exchange apparatus communicating with the sample chamber and with a source of air or gas for introducing the air or gas into the sample chamber to drain sample fluid therefrom, and for discharging the air of gas from the sample chamber to admit sample fluid into the sample chamber from the settling chamber; and a testing device disposed in the sample chamber for testing the sample fluid, and connected to a control and analysis device.

2. Device according to claim 1, characterized in that the control and analysis device is arranged at a distance from the measuring buoy and is operably connected to it.

3. Device according to claim 1, characterized in that the control and analysis device is arranged in the measuring buoy.

4. Device according to claim 1, characterized in that at least one reagent dosing device, which opens into the sample chamber and is connected to a reagent source located outside the measuring buoy via a hose assembly, is arranged in the measuring buoy.

5. Device according to claim 1, characterized in that the gas exchange device comprises a gas pump arranged in the measuring buoy and connected to the sample chamber.

6. Device according to claim 1, characterized in that a fill level sensor, which is connected to the control unit for the gas exchange device, is positioned near the chamber opening connecting the settling chamber to the sample chamber.

7. Device according to claim 1, characterized in that a deflection object, which extends beyond the perpendicular projection of the perimeter of the floor opening on all sides, is positioned at a distance beneath the floor opening.

8. Device according to claim 2, characterized in that the sample chamber is linked to a gas supply line for supplying a reaction gas capable of reacting with waste water, that the chamber opening can be locked by means of a valve, and that a gas discharge line which can be locked by means of a valve runs from the sample chamber to an analysis device located at a distance from the measuring buoy.

9. Device according to claim 1, characterized in that the chamber opening of the sample chamber can be locked by means of a valve.

10. Apparatus for analyzing fluid samples comprising:

a measuring buoy immersible in a body of fluid to be tested, the buoy forming a sample chamber in which samples of the fluid are to be tested, the sample chamber communicating with the body of fluid through a chamber opening;

a gas exchange apparatus communicating with the sample chamber and with a source of air or gas for introducing the air or gas into the sample chamber to drain sample fluid therefrom, and for discharging the air or gas from the sample chamber to admit sample fluid into the sample chamber;

a testing device disposed in the sample chamber for testing the sample fluid, and connected to a control and analysis device; and a drivable rotor arranged in the sample chamber and having an outer surface forming a biological growth surface.

11. Device according to claim 10, characterized in that there is a narrow gap between the outer surface of the rotor and the wall of the sample chamber.

12. Device according to claim 10, characterized in that the sample chamber is in direct contact with the surrounding fluid via the chamber opening and is surrounded by an aeration chamber for dilution water which opens into the sample chamber through an overflow opening.

13. Device according to claim 10, characterized in that the chamber opening of the sample chamber opens into an aeration chamber, which includes an opening for admitting sample fluid, wherein the chamber opening communicates indirectly with the body of fluid.

\* \* \* \* \*